United States Patent
Shin et al.

(10) Patent No.: US 10,740,948 B2
(45) Date of Patent: Aug. 11, 2020

(54) APPARATUS AND METHOD FOR GENERATING THREE-DIMENSIONAL IMAGE OF POLYMER SOLUTE SUBSTANCE WHICH EXISTS IN LIQUID SOLVENT

(71) Applicant: HANBAT NATIONAL UNIVERSITY INDUSTRY-ACADEMIC COOPERATION FOUNDATION, Daejeon (KR)

(72) Inventors: Sang Mo Shin, Daejeon (KR); Jeong Hoh Park, Sejong (KR); Dong Min Kim, Daejeon (KR)

(73) Assignee: HANBAT NATIONAL UNIVERSITY INDUSTRY-ACADEMIC COOPERATION FOUNDATION, Daejeon (KR)

( * ) Notice: Subject to any disclaimer, the term of this patent is extended or adjusted under 35 U.S.C. 154(b) by 209 days.

(21) Appl. No.: 16/068,986

(22) PCT Filed: Jan. 12, 2017

(86) PCT No.: PCT/KR2017/000422
§ 371 (c)(1),
(2) Date: Jul. 10, 2018

(87) PCT Pub. No.: WO2017/123023
PCT Pub. Date: Jul. 20, 2017

(65) Prior Publication Data
US 2019/0035136 A1   Jan. 31, 2019

(30) Foreign Application Priority Data
Jan. 12, 2016  (KR) .................. 10-2016-0003893

(51) Int. Cl.
*G06T 15/00*  (2011.01)
*G01Q 30/04*  (2010.01)
(Continued)

(52) U.S. Cl.
CPC ............ *G06T 15/00* (2013.01); *C12Q 1/68* (2013.01); *G01N 33/68* (2013.01); *G01N 33/92* (2013.01);
(Continued)

(58) Field of Classification Search
None
See application file for complete search history.

(56) References Cited

U.S. PATENT DOCUMENTS 5,497,656 A    3/1996  Kado et al.
5,948,621 A *  9/1999  Turner .............. B01J 19/0046
                                                427/150
(Continued)

FOREIGN PATENT DOCUMENTS

EP    2871242 A1    5/2015
JP    H09236609 A   9/1997
(Continued)

OTHER PUBLICATIONS

Heymann et al., Site-Specific 3D Imaging of Cells and Tissues with a Dual Beam Microscope, Journal of Structural Biology, 2006, pp. 63-73, vol. 155, National Cancer Institute, Bethesda, MD.
(Continued)

*Primary Examiner* — Heather R Jones
(74) *Attorney, Agent, or Firm* — Levenfeld Pearlstein, LLC

(57) ABSTRACT

The present invention relates to an apparatus and method for generating a three-dimensional image of a polymer substance. The three-dimensional image generating apparatus of the present invention comprises: a specimen state adjustor for adjusting a temperature or pressure of a solid specimen in order to maintain, in a solid state, the solid specimen including a plurality of polymer substances; an image collector for collecting a partial image of the plurality of
(Continued)

polymer substances exposed on a surface of the solid specimen; a low molecule image database for storing an image of an element low molecule substance; and an image processor for generating a three-dimensional image of the polymer substance by matching the collected partial image with an image in the low molecule image database.

13 Claims, 6 Drawing Sheets

(51) Int. Cl.
| | |
|---|---|
| G01Q 30/10 | (2010.01) |
| C12Q 1/68 | (2018.01) |
| G01N 33/68 | (2006.01) |
| G01N 33/92 | (2006.01) |
| G01Q 30/20 | (2010.01) |
| G01Q 30/12 | (2010.01) |
| G16Z 99/00 | (2019.01) |
| G06T 7/73 | (2017.01) |
| G01Q 30/16 | (2010.01) |
| G06K 9/62 | (2006.01) |
| G06T 3/00 | (2006.01) |
| G01Q 30/02 | (2010.01) |
| G02B 21/36 | (2006.01) |

(52) U.S. Cl.
CPC .............. *G01Q 30/04* (2013.01); *G01Q 30/10* (2013.01); *G01Q 30/12* (2013.01); *G01Q 30/16* (2013.01); *G01Q 30/20* (2013.01); *G06K 9/6201* (2013.01); *G06T 3/0068* (2013.01); *G06T 7/73* (2017.01); *G16Z 99/00* (2019.02); *G01Q 30/02* (2013.01); *G01Q 30/025* (2013.01); *G02B 21/367* (2013.01); *G06T 2207/10056* (2013.01); *G06T 2207/20221* (2013.01)

(56) References Cited

U.S. PATENT DOCUMENTS

| | | |
|---|---|---|
| 2009/0220130 A1 | 9/2009 | Slingerland |
| 2011/0090500 A1 | 4/2011 | Hu et al. |
| 2015/0063406 A1 | 3/2015 | Mujat et al. |
| 2015/0160114 A1* | 6/2015 | Shin .................. G01N 1/42 435/5 |

FOREIGN PATENT DOCUMENTS

| | | |
|---|---|---|
| KR | 1020140005620 A | 1/2014 |
| WO | 2004036591 A1 | 4/2004 |

OTHER PUBLICATIONS

Kim et al., AFM study of surface phenomena based on C60 film growth, Applied Surface Science, 1998, pp. 302-609, vol. 130-132, Elsevier Science B.V., New York, NY.
Kobayashi et al., Imaging of fullerene molecules on Si(111)-7X7 surface with NC-AFM, Applied Surface Science, 2000, pp. 228-232, vol. 157, Isevier Science B.V., New York, NY.
Hirahara et al., One-Dimensional Metallofullerene Crystal Generated Inside Single-Walled Carbon Nanotubes, Physical Review Letters, Dec. 18, 2000, pp. 5384-5387, vol. 85, No. 25, The American Physical Society, College Park, Maryland.
Klein et al., Ordered stretching of single molecules of deoxyribose nucleic acid between microfabricated polystyrene lines, Applied Physics Letters, Apr. 16, 2001, pp. 2396-2398, vol. 78, No. 16, American Institute of Physics, College Park, MD.
Huang et al., Directed Assembly of One-Dimensional Nanostructures into Functional Networks, Science, Jan. 26, 2001, pp. 630-633, vol. 291, Issue 5504, American Association for the Advancement of Science, Washington D.C.
Ando et al., A high-speed atomic force microscope for studying biological macromolecules, PNAS, Oct. 23, 2001, pp. 12468-12472, vol. 98, No. 22, National Academy of Sciences, Washington D.C.
Moller et al., Tapping-Mode Atomic Force Microscopy Produces Faithful High-Resolution Images of Protein Surfaces, Biophysical Journal, Aug. 1999, pp. 1150-1158, vol. 77, Biophysical Society, Rockville, MD.
Thundat et al., Atomic force microscopy of DNA on mica and chemically modified mica, Scanning Microsc., Dec. 1992, pp. 911-918, vol. 6, No. 4, Oak Ridge National Laboratory, Tennessee.
Hansma et al., Atomic force microscopy of DNA in aqueous solutions, Nucleic Acids Research, 1993, pp. 505-512, vol. 21, No. 3, Oxford University Press, UK.
Murray et al., Atomic force microscopy of biochemically tagged DNA, Biophysics, May 1993, pp. 3811-3814, vol. 90, National Academy of Sciences, Washington D.C.
International Preliminary Report on Patentability issued by IB of WIPO in connection with PCT/KR2017/000422 dated Jul. 17, 2018.
International Search Report issued by ISA/KR in connection with PCT/KR2017/000422 dated May 8, 2017.
Written Opinion issued by ISA/KR in connection with PCT/KR2017/000422 dated May 8, 2017.
European Search Report issued by EPO in connection with EP17738652 dated Jul. 30, 2019.

* cited by examiner

FIG. 7

Ile – Val – Ile – Val – Val
Val – Phe – Tyr – Trp – Thr

Val-Ile-Phe-Val-Tyr-Ile-Trp-Val-Thr-Val

FIG. 8

APPARATUS AND METHOD FOR GENERATING THREE-DIMENSIONAL IMAGE OF POLYMER SOLUTE SUBSTANCE WHICH EXISTS IN LIQUID SOLVENT

TECHNICAL FIELD

The present invention relates to an apparatus and a method of generating a three-dimensional image of a polymer substance which exists in a liquid solvent. More particularly, the present invention relates to an apparatus and a method of generating a three-dimensional image, the apparatus and the method being capable of imaging a polymer in cells.

BACKGROUND ART

In modern molecular biology, it is an important task to identify which molecules and which configuration thereof composes each cell or organelle, which molecules are created, where the molecules are transported, and how the molecules are changed and divided in each organelle. Cellular motility and growth are central to normal physiological processes. When cell motility and growth are restricted, negative consequences such as tumor formation may result.

In particular, it is important to know three-dimensional distributions of polymers or elements constituting a cell and know changes of the three-dimensional distributions for understanding cell structure and function of each organelle. A representative method for identifying the three-dimensional distribution of the polymer or elements constituting the cell is a fluorescence imaging technique.

According to the fluorescence imaging technique, after a target molecule in cells is attached with a fluorescent marker or the molecule is treated to express fluorescence itself by gene manipulation, a fluorescence image allows the three-dimensional distribution of the target molecule to be identified. A confocal laser scanning microscope is a device to which the fluorescence imaging technique is applied. However, when conducting the fluorescence imaging technique, a foreign substance such as a fluorescent gene or a fluorescent marker is required to be introduced into the cell to perform imaging in an artificial state rather than a natural state of the cell itself. In addition, in order to detect a specific molecule by fluorescence imaging, the specific molecule is necessary to exist in a cell at a predetermined concentration or more. Thus, it is impossible to identify a three-dimensional distribution of a molecule having a low concentration of the specific molecule even when the molecule is attached with a marker or genetically manipulated. Further, since a fluorescent image is to be seen, additional steps and analysis are necessary to confirm whether the target molecule is attached to the marker.

As a cell imaging method other than an optical method and a biochemical method, there is a method of studying the structure and constituent molecules of cells and organelles by using a scanning electron microscope (SEM), a transmission electron microscope (TEM), an atomic force microscope (AFM), a scanning tunneling microscope (STM), or the like.

In the case of using an SEM, secondary electrons or back scattered electrons having the highest probability of occurrence among various signals generated in a sample are detected when an electron beam is scanned over a sample surface such that a target specimen is observed. However, it is difficult to image molecules, and it is required that the specimen is frozen and coated with a metal having a high atomic number.

A TEM uses a deflected electron beam and the electron beam which has penetrated a specimen is magnified by an electron lens for observation. However, although molecules are imaged, imaging and analysis take a long time and it is required that the specimen is frozen and thinly sliced.

An AFM is a two-dimensional scanning microscope with a pyramid-shaped probe in contact with a surface of a specimen. In case of using an atomic power microscopy, atomic level imaging is possible for inorganic specimen and metallic specimen. However, in case of cells in which water accounts for 75 to 80% and cells in which growth medium exists externally thereof, a resolving power of the microscopy deteriorates rapidly. In addition, though an AFM has good resolving power, an imaging area thereof is very narrow, and in living cells, a shape of the cells changes spontaneously or under the influence of the probe of the microscope whereby the AFM may have low image reliability. In addition, in order to obtain atomic resolution, it is required that a molecule to be imaged is placed on a flat solid substrate and low-temperature, low-pressure, and vacuum atmosphere is required. Furthermore, with probes used in current AFMs, it is impossible to image molecules large in size and in height, like intracellular polymers.

An STM is a type of scanning probe microscope, which analyzes the shape of the surface of the specimen using tunneling current. An STM is capable of imaging at the atomic level, but it is required to be in vacuum state to operate and required to maintain conductivity whereby imaging is impossible for cells containing a large amount of water.

Accordingly, the inventors of the present invention have developed an apparatus and a method of generating a three-dimensional image of a polymer, in which a process of sequentially removing surfaces of polymers is unnecessary or minimized while making practical imaging of intracellular polymers possible.

DISCLOSURE

Technical Problem

An object of the present invention is to provide an apparatus and a method of generating a three-dimensional image of a polymer solute substance which exists in a liquid solvent.

In addition, another object of the present invention is to provide an apparatus and a method that generate a three-dimensional image of a polymer without requiring a process in which a surface of the polymer is removed sequentially.

Furthermore, still another object of the present invention is to provide an apparatus and a method that generate a three-dimensional image of a polymer in a cell based on a partial image of a low-molecular-weight substance constituting the polymer.

Technical Solution

In order to accomplish the above objects, an apparatus for generating a three-dimensional image of a polymer solute substance which exists in a liquid solvent, the apparatus including: a specimen phase controller controlling temperature or pressure of a solid specimen containing multiple polymer substances in order to keep the solid specimen in a solid state; an image collector collecting a partial image of the multiple polymer substances exposed on a surface of the solid specimen; a low-molecular-weight substance image database storing an image of a low-molecular-weight substance constituting the polymer; and an image processor generating a three-dimensional image of the polymer substances by matching an image registration on the collected partial image to an image from the low-molecular-weight substance image database.

The apparatus may further include a solid specimen fabrication instrument freezing the liquid containing the multiple polymer substances to fabricate the solid specimen. The solid specimen fabrication instrument may freeze the liquid quickly. In addition, the apparatus may further include a microscope serving to find a location of the polymer substances in the solid specimen.

The image collector may be a scanning probe microscope (SPM) provided with a probe. The specimen phase controller may serve to sublimate the surface of the solid specimen such that the number of the polymer substances required for the image registration is exposed on the surface of the solid specimen.

In addition, in order to accomplish the above objects, a method of generating a three-dimensional image of a polymer solute substance which exists in a liquid solvent, the method including: controlling temperature or pressure of a solid specimen containing multiple polymer substances in order to keep the solid specimen in a solid state; collecting a partial image of the multiple polymer substances exposed on a surface of the solid specimen; and generating a three-dimensional image of the polymer substances by matching an image registration on the collected partial image to an image of a low-molecular-weight substance constituting the polymer.

The generating of the three-dimensional image may include: comparing the collected partial image of the polymer substances to a first image of a low-molecular-weight substance image database; when the images are matched resulting from the comparing, configuring the three-dimensional image of the polymer substances referring to a three-dimensional structure of the low-molecular-weight substance which corresponds to the first image; and when the images are not matched resulting from the comparing, comparing the partial image to a second image from the low-molecular-weight substance image database.

The method may further include freezing the liquid containing the multiple polymer substances to fabricate the solid specimen. In addition, the method may further include finding a location of the polymer substances in the solid specimen. Furthermore, the method may further include finding a location of the polymer substances in the solid specimen.

Advantageous Effects

According to the present invention, because an individual monomer is identified from an entire image of a solute molecule (for example, polymers in cells) existing in a solvent, the entire image resulting from an image registration, it is possible to understand a sequence of the biomolecule such that the monomer of the biomolecule is determined, and sequence information and chemical modification (phosphorylation, methylation, acetylation, oxidation, reduction, and the like) are identified. In addition, when two molecules interacting with each other during a quick freezing process exist in a sample, dozens to hundreds of instantaneous moments in various situations are imaged, so it is possible to monitor the reaction process between two molecules by collecting multiple images of the same molecules. Furthermore, once the above information is obtained, target information for new drug is obtained accurately such that a design for the new drug becomes easier and it is possible to know visually whether the new drug works well on a target, whereby the present invention contributes to the breakthrough of new drug development.

DESCRIPTION OF DRAWINGS

FIG. 7 is a diagram illustrating a structure of a three-dimensional imaging apparatus according to the present invention;

FIG. 8 is a conceptual diagram illustrating a method of identifying an entire amino acid sequence by obtaining a two-dimensional partial image of polymer substances, according to the present invention.

MODE FOR INVENTION

Hereinbelow, preferred embodiments of the present invention will be described with reference to accompanying drawings.

Figure 1:
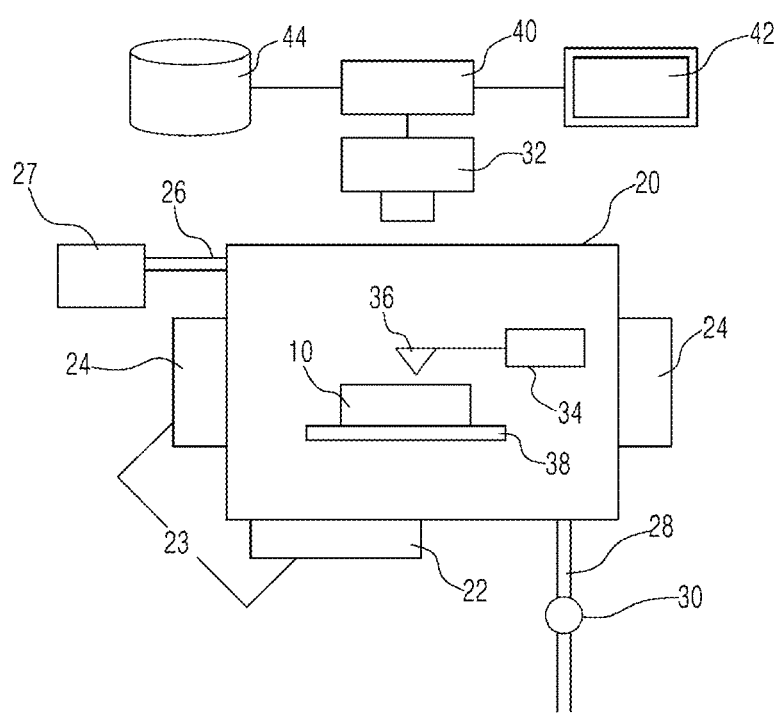
FIG. 1 is a schematic view illustrating a three-dimensional image generating apparatus according to an embodiment of the present invention.
Figure 2:
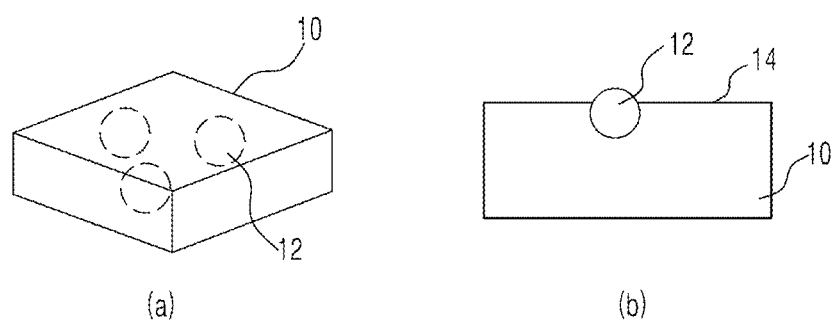
FIG. 2 depicts diagrams illustrating a solid specimen used in the apparatus of FIG. 1.

FIG. 1 is a schematic view showing a three-dimensional generating apparatus according to an embodiment of the present invention. FIG. 2 is a diagram illustrating a solid specimen 10 used in the apparatus of FIG. 1.

The solid specimen 10 is prepared by freezing, particularly, quickly freezing a liquid containing multiple polymer substances. A quick freezer transforms water in polymer substances, the inside and the outside of viruses, or on surfaces into non-crystalline ice. If it is possible to freeze only multiple polymer substances 12, only the multiple polymer substances may be frozen, but in practice, generally the biological fluid or growth medium containing the multiple polymer substances 12 is quickly frozen.

When freezing water quickly, water is not transformed into crystalline ice but into vitrified ice or noncrystalline ice such that the polymeric material 12 is not deformed from a natural form. Thus, it is possible to observe the multiple polymer substances 12 in a natural state. With respect to quickly freezing biological fluid or growth medium containing the multiple polymer substances 12, it may be considered that the biological fluid or the growth medium is placed in a container or a tray having a small volume such as a Petri dish and quickly frozen.

The solid specimen 10 is transferred to an observation chamber 20. The inside of the observation chamber 20 is kept at ultralow temperature which is under freezing point by using liquid nitrogen, liquid helium, and the like to prevent thawing of the solid specimen 10. In addition, when vapor exists inside the observation chamber 20, vapor may be attached inside the observation chamber 20 or an apparatus for imaging in a frozen state. Thus, it is preferable that the inside of the observation chamber 20 is maintained in a vapor-removed state, for example, a nitrogen atmosphere.

An optical microscope 32 may be provided above the observation chamber 20. The optical microscope 32 serves to obtain an optical image of the specimen 10. An electron microscope may be provided instead of the optical microscope 32. The optical microscope 32 serves to obtain an image of an upper portion of the solid specimen 10 at the atomic level. The reason for providing the optical microscope 32 is to check an image of the solid specimen 10 and then to locate approximate position and relative position of multiple polymer substances or viruses, which are actual objects to be observed, on the solid specimen 10.

Noncrystalline ice is in a solid state whereby it is possible to image objects at the molecular or atomic level by using an atomic force microscope (AFM) or a scanning tunneling microscope (STM). Accordingly, it is preferable that a surface measuring instrument 34 is provided inside the observation chamber 20, the surface measuring instrument 34 scanning an upper surface of the solid specimen 10 to generate an image thereof. A scanning probe microscope (SPM) may be used as the surface measuring instrument 34 and different modes of AFM may be used, the scanning probe microscope (SPM) being capable of scanning a surface of the solid specimen 10 at the atomic level. The AFM falls into contact mode and non-contact mode depending on whether the solid specimen 10 and the probe 36 are in contact. In order to scan the surface and the flexure of the solid specimen 10, an attraction force (van der Waals force) between the probe 36 and the surface of the solid specimen 10 in case of the contact mode, or a repulsion force between the probe 36 and the surface of the solid specimen 10 in the case of the non-contact mode is measured such that information about the surface of the solid specimen 10 is obtained. In case of the contact mode, the solid specimen 10 may be damaged due to the nature of the detection method, thus a tapping mode AFM may be used for overcoming such a drawback. In addition, an STM may be used as the surface measuring instrument 34.

When using the surface measuring instrument 34 such as an AFM and an STM with respect to the quickly frozen specimen 10 as described above, it is possible to image a minute polymer molecule. In addition, it is also possible to image molecular cancer marker, and the like which are present in blood in a very small amount and can not be detected by conventional techniques. Furthermore, when using an AFM, an STM, and the like to scan the surface of the specimen, it is also possible to image a minute three-dimensional shape.

However, the partial image of the surface of the solid specimen 10 obtained in the above process is substantially regarded as a two-dimensional image having three-dimensional information, not a three-dimensional image of a polymer. In order to obtain a three-dimensional image of a polymer molecule, a three-dimensional image is obtained by combining individual two-dimensional images in which various motions of the polymer are exposed on the surface while doing thermal motion in free directions in a liquid, using an image registration algorithm.

When the number of polymer molecules exposed to the surface does not reach a sufficient number of samples for using the image registration algorithm, an already imaged layer may be removed from the solid specimen 10 by sublimation or the like such that an image of a next layer may be obtained. At this point, because the length of the probe 36 is insufficient for the polymer where the image is already obtained from the surface before sublimation, re-acquisition of the image is difficult and instead, an image is obtained from a new polymer molecule exposed due to sublimation.

As a method of removing the surface of the solid specimen 10, it may be considered that the temperature and/or pressure inside the observation chamber 20 is adjusted to sublimate and remove the noncrystalline ice on the surface of the solid specimen 10. In the water phase diagram, only ice and water vapor exist at the temperature or pressure below the triple point. Thus, when raising the temperature while keeping the pressure constant below the triple point, ice sublimates into water vapor. In addition, when lowering the pressure while keeping the temperature constant below the triple point, ice sublimates into water vapor. It is obvious that it is possible to sublimate ice into water vapor by adjusting the temperature and the pressure together below the triple point. Accordingly, the frozen surface of the specimen 10 is removed by adjusting the temperature and the pressure as described above. A heater 22 and a cooler 24 are attached to the observation chamber 20 to control the temperature.

In addition, a vacuum pump 30 is provided for pressure control, the vacuum pump 30 connected to the inside of the observation chamber 20. Meanwhile, in order to remove gases including water vapor undergoing the sublimation inside the observation chamber 20 and to supply gas not including water vapor, the observation chamber 20 is provided with a gas outlet 28 and a gas inlet 26 through which nitrogen and the like are supplied. In one embodiment, the gas outlet 28 may be connected to the vacuum pump 30.

FIG. 2(*b*) shows a state where a very thin layer of the surface of the solid specimen 10 is removed as described above. As described above, a very thin layer of a surface 14 of the solid specimen 10 is removed such that a partial image of elements constituting biomolecules by using the optical microscope 32 and/or the surface measuring instrument 34.

A solidifying means, a temperature/pressure controller, and a surface measuring instrument may be disposed in various ways. For example, the solidifying means may be disposed in a same chamber with other means or disposed in a separate chamber from other means. The temperature/pressure controller may be disposed in a same chamber with the surface measuring instrument or in a separate chamber with the surface measuring instrument. As described in FIG. 7, it is preferable that the temperature/pressure controller and the surface measuring instrument are disposed together in one chamber, that is, the observation chamber 20 which is separate from the solidifying means (for example, refrigeration device). The observation chamber 20 stores the solid specimen 10 in which biopolymers are frozen quickly. In order to maintain an atmosphere in which water vapor is removed, the observation chamber 20 is provided with the gas inlet 26 at one side thereof, the gas inlet 26 communicating with a dehumidified gas supplier 27 which maintains air to be dehumidified or maintains a nitrogen atmosphere. In addition, the observation chamber 20 is provided with the gas outlet 28 at a lower portion thereof, the gas outlet 28 discharging gas inside the observation chamber 20 to the outside therethrough. Furthermore, the observation chamber 20 is provided with a specimen table 38 on which the solid specimen 10 is placed, at the center portion thereof.

Meanwhile, the observation chamber 20 is provided with a temperature controller 23 controlling the temperature of the observation chamber 20. The temperature controller 23 is configured with the heater 22, the cooler 24, and the like, and increases and decreases the temperature inside the observation chamber 20. In addition, the observation chamber 20 is connected to a pressure controller 30 to control the pressure of the observation chamber 20. The pressure controller 30 may be provided as a vacuum pump. The temperature controller 23 and the pressure controller 30 constitute a specimen phase controller that controls a phase of the solid specimen 10.

With above configuration, it is possible to control thawing of the solid specimen 10 by controlling the temperature and/or pressure of the observation chamber 20 while the solid specimen 10 is positioned inside the observation chamber 20. In particular, while the temperature or pressure of the observation chamber 20 are kept below those of the triple point, ice on an upper surface of the solid specimen 10 is sublimated into water vapor by controlling temperature or pressure such that the ice is removed. The interior gases of the observation chamber 20 including the sublimated water vapor are discharged through the gas outlet 28, and dehumidified gas is supplied to the inside of the observation chamber 20 through the gas inlet 26.

The observation chamber 20 is provided with the surface measuring instrument 34, and the surface measuring instrument 34 may be an AFM or an STM. A probe 36 of an AFM or an STM is located inside the observation chamber 20 and scans an upper surface of the solid specimen 10. In addition to scanning the upper surface of the solid specimen 10, it is possible that the probe 36 is used to remove a cell component of an upper portion of the solid specimen 10, if necessary. The surface measuring instrument 34, the probe 36, and the like constitutes an image collector which collects partial images of multiple polymer substances which are exposed on the surface of the solid specimen 10.

The image processor 40 generates a two-dimensional image of the surface of the solid specimen 10 by processing the information of the surface of the solid specimen 10 measured by the probe 36 of the surface measuring instrument 34. Preferably, the image processor 40 is connected to the visual display apparatus 42 and shows the processed two-dimensional image.

As described above, according to the embodiment of the present invention, it is possible to obtain a variety of two-dimensional images of the various angles of the biopolymers exposed on the surface of the solid specimen 10. It is possible for the image processor 40 to generate a three-dimensional image of the biopolymers by matching an image registration on the obtained multiple partial images of the solid specimen 10 with an image of a low-molecular-weight substance image database 44 which stores an image of a low-molecular-weight substance constituting the polymer.

Figure 3:
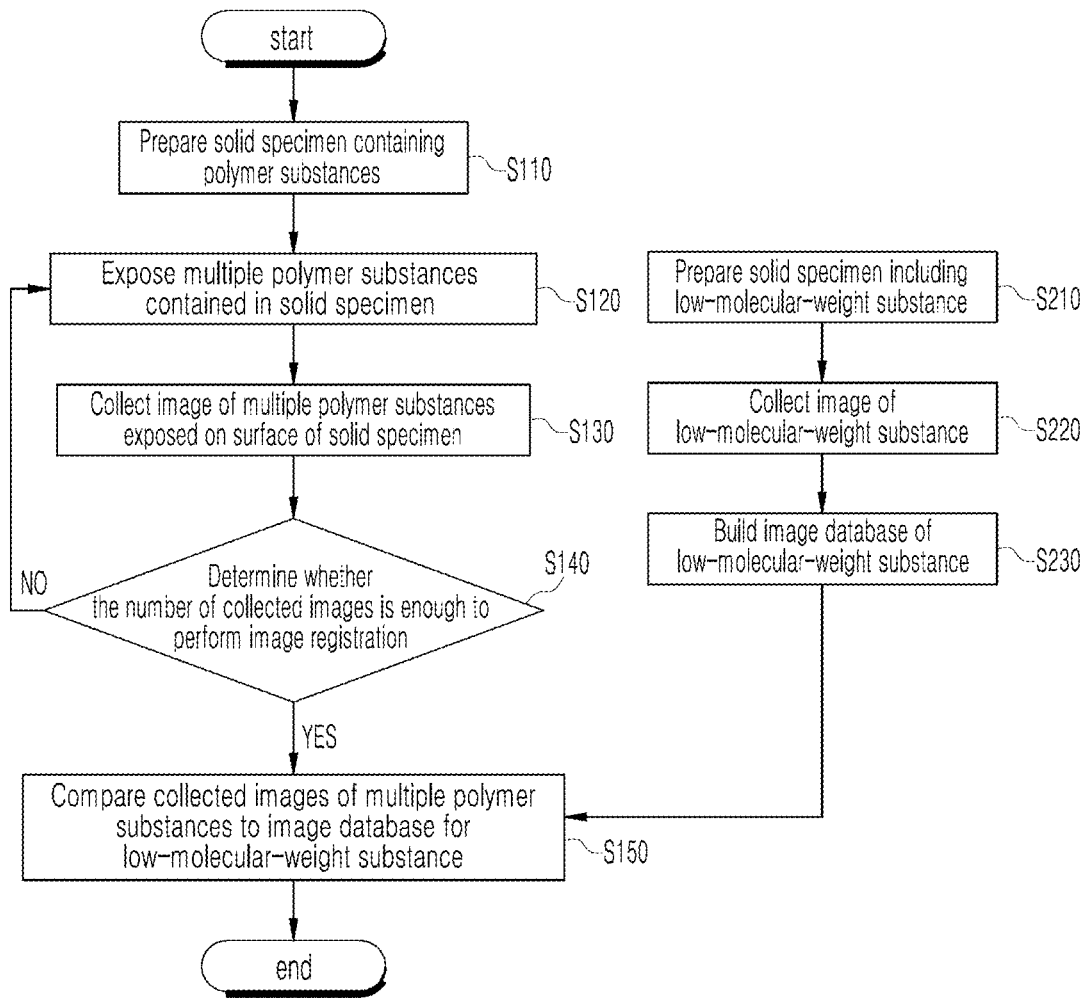
FIG. 3 is a process flow diagram illustrating a method of generating a three-dimensional molecular image of a polymer substance according to an embodiment of the present invention.
Figure 4:
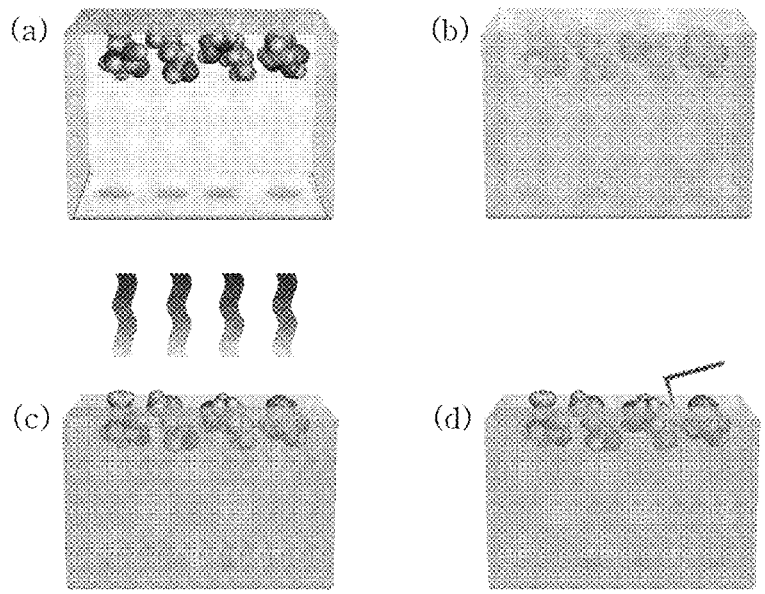
FIG. 4 depicts diagrams illustrating the method of generating a three-dimensional molecular image of a polymer substance according to the embodiment of the present invention.
Figure 5:
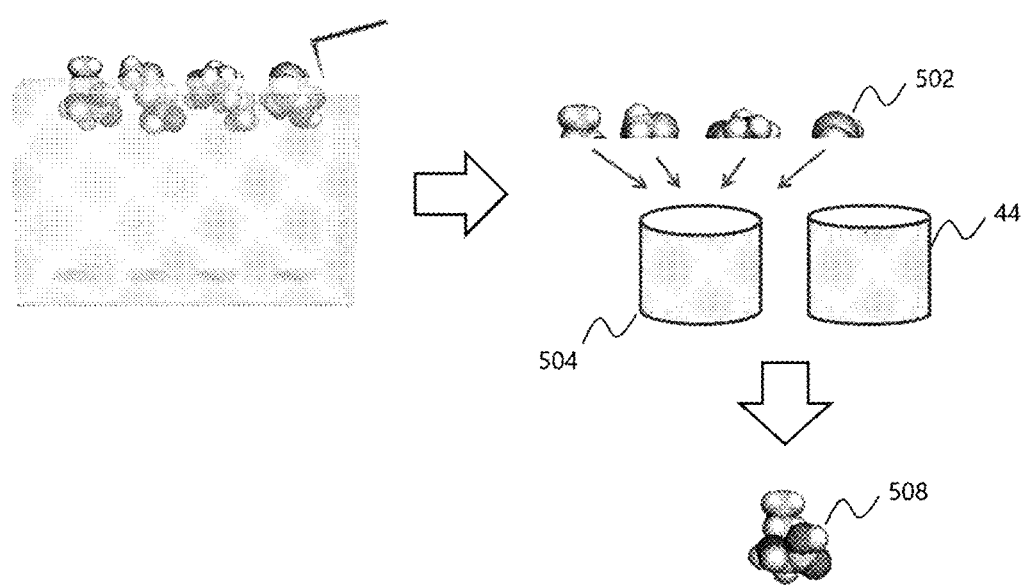
FIG. 5 is a diagram illustrating a process in which a three-dimensional image of entire polymer substance is determined according to the embodiment of the present invention.

FIG. 3 is a process flow diagram illustrating a method of generating a three-dimensional molecular image of a polymer substance according to an embodiment of the present invention. FIG. 4 depicts diagrams illustrating the method of generating a three-dimensional molecular image of a polymer substance according to the embodiment of the present invention. In detail, FIG. 4(a) shows a state in which a polymer substance to be imaged in three-dimension is melted in a liquid, FIG. 4(b) shows a state in which the polymer substance is frozen in a natural state by a quick freezing process, FIG. 4(c) shows a process in which the polymer substance to be imaged is exposed on a surface by sublimation, and FIG. 4(d) shows a process in which an image of the surface is collected by using an SPM, and the like, provided with a probe. FIG. 5 is a diagram illustrating a process in which a partial image 502 of a low-molecular-weight substance constituting the polymer substance to be imaged in three-dimension is collected and stored at a specimen image database 504, an image registration algorithm is performed on the collected image with an image from the low-molecular-weight substance image database 44 such that a three-dimensional image 508 of the entire polymer substance is determined.

(1) Preparing a Solid Specimen

In the embodiment, a solid specimen is prepared by freezing a liquid containing one kind of multiple polymer substances (S110). FIGS. 4(a) and 4(b) illustrate the step.

Liquids containing the polymer substances include growth medium, buffer, and biological fluid used for separation and extraction of polymers, but is not limited thereto.

The embodiment may be applied to proteins, lipids, polysaccharides, nucleic acid, and various biopolymers, and the solid specimen is prepared by using various biopolymers described above and a liquid containing them. According to the embodiment, it is possible to image viruses composed of biopolymers. Viruses to be imaged include animal viruses, plant viruses, and bacteriophage. For example, hepatitis B virus (HBV), hepatitis C virus (HCV), hepatitis A virus (HAV), human immunodeficiency virus (HIV), reovirus, Sendai virus, myxovirus, coronavirus, encephalomyelitis virus, rotavirus, cytomegalovirus, measles virus, vaccinia virus, rabies virus, Epstein-Barr virus, rhinovirus, polio virus, herpes virus, and the like may be imaged according to the present invention, but not limited thereto.

The solid specimen may be prepared by various freezing methods known in the art. For example, the freezing may be performed in a temperature range of $-200°$ C. to $-15°$ C., in a temperature range of $-180°$ C. to $-20°$ C., in a temperature range of $-150°$ C. to $-35°$ C., and in a temperature range of $-200°$ C. to $-55°$ C.

For example, the freezing may be performed by impregnating a container containing a target polymer or a solution in which a target polymer is resolved with a mixture of solid carbon dioxide and alcohol or liquid nitrogen. The mixture of solid carbon dioxide and alcohol or liquid nitrogen may be contained in a container. The container may be positioned directly in a freezer, and the freezer may be set at a desired temperature (for example, equal to or below $-35°$ C.). The freezer may be a programmable freezer or a freezer whose freezing speed is controlled. The solid specimen may be stored at a temperature equal to or below the temperature at which recrystallization occurs, for example, equal to or below the glass transition temperature of pure water (for example, $-135°$ C.).

It is preferable to perform quick freezing by using liquid nitrogen. The definition, "quick freezing", in the description generally means that a liquid is cooled by rapidly passing the maximum ice crystallization region (for example, $-5°$ C. to $-1°$ C., equal to or more than 80% of solidification) within the minimum period (for example, within a range of 30 minutes to 35 minutes) in order to make a size of ice crystal small or to obtain noncrystalline ice (or vitrified ice). Quick freezing includes a vitrification method.

Since the solid specimen is solid, it is possible that a suitable imaging instrument, for example, an AFM or an STM, is used to image the specimen at the atomic/molecular level. Because non-crystalline ice melts at room temperature, it is preferable to image the specimen at the temperatures equal to or below the freezing point. In addition, when imaging at an room pressure and at low temperatures, because the moisture in the air may be frozen on a portion of the imaging instrument which is maintained low temperatures, it is preferable to image in a dehumidified atmosphere (for example, in nitrogen atmosphere).

(2) Providing a Surface to be Imaged by Removing the Surface of the Solid Specimen In order to collect a two-dimensional image of the surface of the solid specimen, the surface of the solid specimen is removed expose a surface to be imaged (S120). FIG. 4(c) illustrates the step.

In the embodiment, removing the surface of the solid specimen is performed by sublimating ice on the surface of the solid specimen. Water in a living body (for example, cell, tissue, body fluid, and blood) occupies equal to or more than 80% of the volume thereof. It is required that the ice formed during the fabrication of the solid specimen, more desirably, noncrystalline ice is removed while minimizing damage to the specimen such as polymer. Accordingly, in the embodiment, the ice on the surface of the solid specimen is subliminated.

Sublimation may be performed by controlling a pressure at a constant temperature below the triple point. The pressure control may be performed by a vacuum pump or a cold trap. Alternatively, sublimation may be performed by controlling a temperature at a constant pressure below the triple point. A temperature control for sublimation may be accomplished by using a heater and a cooler, or by heating an SPM probe used for obtaining a surface image to partially control the temperature.

In the water phase diagram, only ice and water vapor exist at the temperature or pressure below the triple point. Thus, when raising the temperature while keeping the pressure constant below the triple point, ice sublimates into water vapor. In addition, when lowering the pressure while keeping the temperature constant below the triple point, ice sublimates into water vapor. In such a manner, ice on the surface of the solid specimen is removed by sublimation such that a surface on which one kind of multiple polymer substances to be subjected to surface information collection are exposed is provided. At this point, because the one kind of multiple polymer substances has various relative positions due to thermal motion, an exposed portion of the multiple polymer substances appears variously.

When removing the surface of the solid specimen, ice is removed by sublimation and the polymers having large molecular weight remain instead of being sublimated. When imaging the remaining polymers, it is possible to obtain individual and partial images from the low-molecular-weight substances constituting the polymer.

With respect to the steps (1) and (2), it is also possible that the volume of the liquid containing the polymer substances is minimized such that the multiple polymer substances are directly exposed from the ice surface of the solid specimen at the freezing step.

(3) Collecting a Partial Image which is Information of the Surface

Information of the surface of the solid specimen which is prepared by solidifying the liquid containing the polymers is collected (S130). FIG. 4(d) illustrates the step.

It is preferable to collect information of the surface of the solid specimen by using an SPM provided with a probe. An SPM is a tool for measuring physical properties of a subject in a micrometer and/or nanometer scale. The SPM is provided with a probe, which is located close to a surface of the subject. The probe may be mounted on a cantilever having a length of a few hundred micrometers and a thickness from 0.5 μm to 5 μm. A method of using an SPM is disclosed in Wang et al., Amer. Chem. Soc. Lett., 12:1697-98. 1996; Kim et al., Appl. Surface Sci. 130, 230, 340-132:602-609, 1998; Kobayashi et al., Appl. Surface Sci. 157:228-32, 2000; Hirahara et al., Phys. Rev. Lett. 85:5384-87, 2000; Klein et al., Applied Phys. Lett. 78:2396-98, 2001; Huang et al., Science 291:630-33, 2001; and Ando et al., Proc. Natl. Acad. Sci. USA 12468-72, 2001.

Preferably, an SPM used to collect information of the surface in the embodiment is an atomic force microscope (AFM), a scanning tunneling microscope (STM), a ballistic electron emission microscope (BEEM), a chemical force microscope (CFM), a conductive atomic force microscope (C-AFM), an electrostatic force microscopy (EFM), an electrochemical scanning tunneling microscope (ESTM), a force modulation microscope (FMM), a Kelvin probe force microscope (KPFM), a magnetic force microscope (MFM), a magnetic resonance force microscope (MRFM), a near-field scanning optical microscope (NSOM), a scanning near-field optical microscope (SNOM), a piezoresponse force microscope (PFM), a photon scanning tunneling microscope (PSTM), a photothermal microscope (PTMS), a scanning electrochemical microscope (SECM), a scanning capacitance microscope (SCM), a scanning gate microscope (SGM), a scanning ion-conductance microscope (SICM), a spin polarized scanning tunneling microscope (SPSM), a scanning spreading resistance microscope (SSRM), a scanning thermal microscope (SThM), a scanning voltage microscope (SVM), a scanning tunneling potentiometry (STP), a scanning Hall probe microscope (SHPM), or a synchrotron x-ray scanning tunneling microscope (SXSTM), and more preferably, an AFM or an STM is used, and most preferably, an AFM is used.

A method of using an AFM is disclosed in U.S. Pat. No. 5,497,656; Moller et al., Biophys. J., 77:1150-8, 1999; Thundat [0056] et al., Scanning Microsc. 6:911-8, 1992; Hansma et al., Nucleic Acids Res., 21:505-12, 1993; and Murray et al., Proc. Natl. Acad. Sci. USA, 90:3811-4, 1993.

The collection of surface information is performed by measuring a force between the surface of the solid specimen and the probe (desirably, Van der Waals force). It is possible to obtain the surface state of the polymers to be analyzed and information (for example, three-dimensional image) from the low-molecular-weight substances constituting the polymers due to the collection of the surface information.

When a predetermined number of partial images (meaning, surface information) that are required to obtain a three-dimensional image of the polymer substances are not obtained (S140), the steps (2) and (3) may be repeated.

(4) Obtaining Three-Dimensional Image of the Polymer by an Image Registration

A partial image from the low-molecular-weight substances constituting the polymer substances to be imaged in three-dimension is collected by the same process as the obtainment of the polymer image or by the existing SPM measurement process, and stored in the specimen image database 504 as shown in FIG. 5. Then, a three-dimensional image 508 of the entire polymer substances is determined by an image registration algorithm referring to the low-molecular-weight substance image database 44 (S150).

The solid specimen may contain at least thousands of polymers substantially. Thus, integrating all the partial information collected individually may yield a three-dimensional image of the cell component excluding water in the cell, and may confirm the relation among the cell components.

A conventional amino acid database, a fatty acid database, a monosaccharide database, and a nucleic acid database may be used as the low-molecular-weight substance image database 44. Alternatively, an image database for a low molecular substance in which a solid specimen containing the low-molecular-weight substance is prepared and an image from the low-molecular-weight substance is collected may be used.

Figure 6:
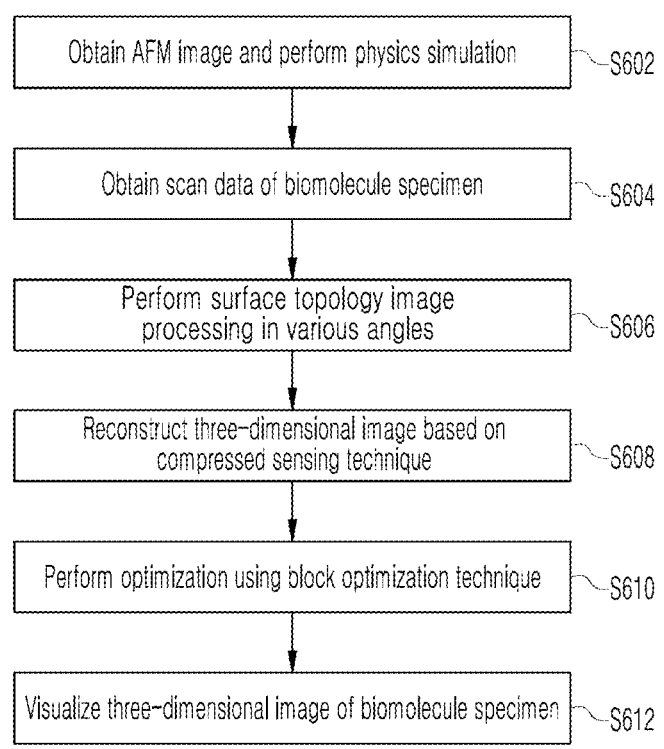
FIG. 6 is a conceptual diagram illustrating an image registration algorithm according to an embodiment of the present invention.

FIG. 6 is a flow diagram illustrating an image registration algorithm in which the polymer substances are visualized in three-dimensional image by the partial image from the low-molecular-weight substance (specimen scan data) and physics simulation.

An AFM image is obtained and physics simulation is performed to obtain a base structure (S602), and supplemented with scandata (the partial image obtained at the previous step) of the biopolymers specimen (S604). When obtaining raw data from the AFM, an atom image does not appear immediately such that simulation is performed according to density functional theory (DFT) to obtain a familiar atom image. Then, a surface topology image processing is performed in various angles referring to the low-molecular-weight substance image database 44 (S606). At the step, the atom image obtained from the previous step is rotated with respect to X, Y, and Z axes to perform image processing in various angles. Then, a three-dimensional image is reconstructed from the obtained image based on a compressed sensing technique (S608). Then, an optimization process is performed using block optimization technique (S610) whereby a three-dimensional image of the biopolymers is obtained and visualized (S612).

According to the present invention, three-dimensional images of various polymer substances such as a receptor and a channel on a cell membrane surface, a cell membrane protein, a cell membrane surface carbohydrate, a cell surface marker, a cell organelle, a chromosome, a protein (for example, enzyme, antibody, antigen, structural protein, hormone, growth factor, and serum protein), a nucleic acid molecule (for example, DNA, RNA, mRNA, rRNA, tRNA, miRNA, and siRNA), a carbohydrate, and a lipid may be provided. In addition, according to the present invention, an image (particularly, three-dimensional image) of an inside and a surface of virus constituting of polymers such as a protein, a nucleic acid, a lipid may be provided.

FIG. 7 is a conceptual diagram illustrating a configuration of an apparatus for imaging a surface atomic structure of polymer substances in three-dimension according to another embodiment of the present invention.

A pre-chamber 702 serves to fabricate the solid specimen. In the pre-chamber 702, a polymer solution is sprayed by an atomizer 706 and distributed in a nano-well plate 708 having a small unit volume such that the polymer solution is cooled quickly. The nano-well plate 708 is disposed on a cold stage 710. The specimen solidified in the pre-chamber 702 is moved to an observation chamber 704 by a loader 712. An AFM cantilever 716 which is an AFM equipment and a piezo-scanner 714 are provided in the observation chamber 704 and perform imaging of the polymer surface.

According to the present invention, information of various biopolymers existing on a surface of a cell and existing inside a cell, and also, information of an atomic structure of the surface may be obtained. In addition, information of an interaction among the biomolecules and an organic relation among the cell organelles may be understood effectively.

For example, after obtaining a partial image to identify a surface atomic structure of a particular protein as shown in FIG. 8, it is possible to know a sequence of an amino acid residue exposed to a surface of the particular protein from the partial image, whereby it is possible to understand an amino acid sequence of the entire protein with a high probability by combining the obtained sequence information.

In addition to protein and amino acid sequences, it is possible to understand a sequence of a biomolecule to identify monomers of the biomolecule, as well as to identify sequence information and chemical modifications of elements (phosphorylation, methylation, acetylation, oxidation, reduction, and the like).

In addition, when two molecules interacting with each other during quick freezing process exist in a sample, instantaneous images of various situations are generated, so it is possible to monitor the reaction process between two molecules by collecting multiple images of the same molecules.

Figure 9:
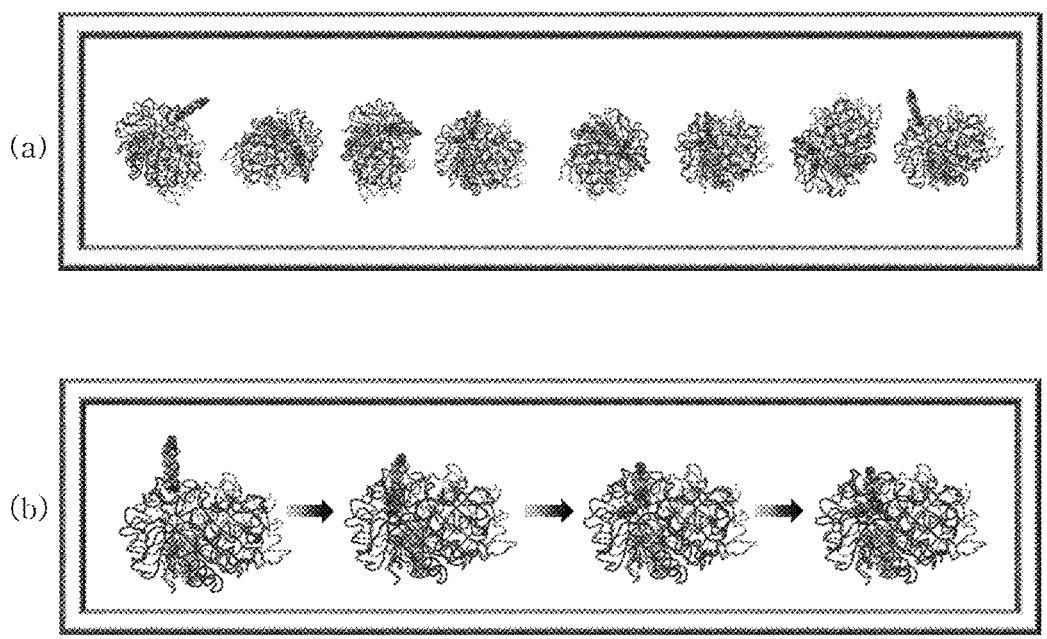
FIG. 9 depicts conceptual diagrams illustrating a method obtaining multiple two-dimensional partial images of polymer substances and identifying changes in a three-dimensional structure of the polymer substances when the polymer substances are combined with enzyme inhibitor or accelerator, according to the present invention.

FIG. 9 depicts conceptual diagrams illustrating a method obtaining multiple two-dimensional partial images of the polymer substances and identifying changes in a three-dimensional structure of the polymer substances when the polymers are combined with an enzyme inhibitor or accelerator, according to the present invention.

The various two-dimensional partial images of the polymer substances are obtained as shown in FIG. 9(a), and changes in a three-dimensional structure of the polymer substances are identified sequentially as shown in FIG. 9(b) when the polymer substances such as enzymes are combined with enzyme inhibitor or accelerator. When two molecules interacting with each other exist in a solid specimen originated from the liquid, dozens to hundreds of instantaneous moments in various situations are partially imaged, so it is possible to monitor the reaction process between two molecules by collecting multiple images of the same molecules.

Once the above information is obtained, target information for new drug is obtained accurately such that a design for the new drug becomes easier and it is possible to know visually whether the new drug works well on a target, whereby the present invention contributes to the breakthrough of new drug development.

In addition to the above-mentioned examples, the present invention is also widely applicable to basic research on polymers in cells, and researches on interactions between polymer substances produced by germs and substances in cells, effects of drug and chemical substances on cells, polymers involved in cell differentiation and replication, and the like.

Although the preferred embodiment according to the present invention have been disclosed for illustrative purposes. It is thus well known to those skilled in that art that the present invention is not limited to the embodiment disclosed in the detailed description, and the patent right of the present invention should be defined by the scope and spirit of the invention as disclosed in the accompanying claims. Accordingly, it should be understood that the present invention includes various modifications, additions and substitutions without departing from the scope and spirit of the invention as disclosed in the accompanying claims.

The invention claimed is:

1. An apparatus for generating a three-dimensional image of a polymer solute substance which exists in a liquid solvent, the apparatus comprising:
a specimen phase controller controlling temperature or pressure of a solid specimen containing multiple polymer substances in order to keep the solid specimen in a solid state;
an image collector collecting a partial image of the multiple polymer substances exposed on a surface of the solid specimen;
a low-molecular-weight substance image database storing an image of a low-molecular-weight substance constituting the polymer; and
an image processor generating a three-dimensional image of the polymer substances by matching an image registration on the collected partial image to an image from the low-molecular-weight substance image database.

2. The apparatus of claim 1, further comprising:
a solid specimen fabrication instrument freezing the liquid containing the multiple polymer substances to fabricate the solid specimen.

3. The apparatus of claim 2, wherein the solid specimen fabrication instrument freezes the liquid quickly.

4. The apparatus of claim 1, wherein the image collector is a scanning probe microscope (SPM) provided with a probe.

5. The apparatus of claim 1, further comprising:
a microscope serving to find a location of the polymer substances in the solid specimen.

6. The apparatus of claim 1, wherein the specimen phase controller serves to sublimate the surface of the solid specimen to expose the polymer substances.

7. The apparatus of claim 6, wherein the specimen phase controller performs an additional sublimation on the solid specimen when the number of the polymer substances required for the image matching is not exposed on the surface of the solid specimen.

8. The apparatus of claim 1, wherein the image processor performs:
comparing the collected partial image of the polymer substances to a first image from the low-molecular-weight substance image database,
when the images are matched resulting from the comparing, configuring the three-dimensional image of the polymer substances referring to a three-dimensional structure of the low-molecular-weight substance which corresponds to the first image, and
when the images are not matched resulting from the comparing, comparing the partial image to a second image from the low-molecular-weight substance image database.

9. The apparatus of claim 1, further comprising:
sublimating the surface of the solid specimen to expose the polymer substances.

10. A method of generating a three-dimensional image of a polymer solute substance which exists in a liquid solvent, the method comprising:
controlling temperature or pressure of a solid specimen containing multiple polymer substances in order to keep the solid specimen in a solid state;
collecting a partial image of the multiple polymer substances exposed on a surface of the solid specimen; and
generating a three-dimensional image of the polymer substances by matching the collected partial image to an image of a low-molecular-weight substance constituting the polymer.

11. The method of claim 10, wherein the generating of the three-dimensional image includes:
comparing the collected partial image of the polymer substances to a first image from a low-molecular-weight substance image database;
when the images are matched resulting from the comparing, configuring the three-dimensional image of the polymer substances referring to a three-dimensional structure of the low-molecular-weight substance which corresponds to the first image; and
when the images are not matched resulting from the comparing, comparing the partial image to a second image from the low-molecular-weight substance image database.

12. The method of claim 10, further comprising:
freezing the liquid containing the multiple polymer substances to fabricate the solid specimen.

13. The method of claim 10, further comprising:
finding a location of the polymer substances in the solid specimen.

* * * * *